United States Patent [19]
Kotliar

[11] Patent Number: 5,850,833
[45] Date of Patent: Dec. 22, 1998

[54] APPARATUS FOR HYPOXIC TRAINING AND THERAPY

[76] Inventor: Igor K. Kotliar, P.O. Box 2021, New York, N.Y. 10159-2021

[21] Appl. No.: 445,677

[22] Filed: May 22, 1995

[51] Int. Cl.$^6$ .................................................. A61G 10/00
[52] U.S. Cl. .............................. 128/202.12; 128/205.11; 128/205.12
[58] Field of Search ..................... 128/202.12, 202.16, 128/205.12, 205.26, 204.22, 205.11, 203.25

[56] References Cited

U.S. PATENT DOCUMENTS

| | | | |
|---|---|---|---|
| 911,528 | 2/1909 | Shoemaker | 128/205.26 |
| 1,224,180 | 5/1917 | Lake | 128/205.26 |
| 2,373,333 | 4/1945 | Onge | 128/202.12 |
| 5,101,819 | 4/1992 | Lane | 128/205.26 |
| 5,383,448 | 1/1995 | Tkatchouk et al. | 128/205.12 |

*Primary Examiner*—Aaron J. Lewis

[57] ABSTRACT

An apparatus is provided for hypoxic training or therapy. The apparatus provides a user air having a lower oxygen content than the ambient atmosphere. The apparatus reduces the oxygen content of the air by passing the ambient air through a membrane separator which extracts the oxygen therefrom by a vacuum pump attached to the permeate outlet of the separator. Alternatively, the oxygen content can be reduced by adsorption of oxygen from the ambient air or by adding a low oxygen gas to air taken from the environment. This low oxygen gas may be stored nitrogen or stored gas which is low in oxygen, or it may be derived from the exhaled air from the user. If the exhaled air from the user used, carbon dioxide and water are extracted by a membrane separator or by physical or chemical process which adsorbs carbon dioxide from the gas.

21 Claims, 4 Drawing Sheets

APPARATUS FOR HYPOXIC TRAINING AND THERAPY

FIELD OF THE INVENTION

The present invention relates to apparatus for providing oxygen-depleted air to a user whereby a low-oxygen mountain air of different altitudes is simulated, and more particularly, to such an apparatus which regulates oxygen content, humidity, temperature and periodity of the oxygen-depleted air being delivered for inhaling by a user.

The wholesome influence of an oxygen-depleted mountain air on humans has been known and used for more than a thousand years, starting with doctors in medieval Europe, tribes in South America and Tibetan monks, all of whom employed this effect to cure their patients or make their chiefs stronger and healthier than others.

A fundamental study of a hypoxic (low-oxygen) training and therapy, taking place for over two decades, mainly in Russia, shows that the periodic inhalation of the oxygen-depleted gas mixtures using a special method increases physical and mental capacities and resistance of the human organism.

Periodic Hypoxic Training (PHT) activates the immune system and protective forces of the organism, and is used for medical, health and fitness purposes. PHT is a drug-free alternative for treatment and prevention of cardiopulmonary, gastrointestinal, gynecological, skin and ocular diseases, as well as various types of allergy, neurological disturbances, and other diseases. PHT is also successfully used for increasing strength, endurance, vitality and resistance to various diseases of healthy people and athletes.

DESCRIPTION OF THE PRIOR ART

European Patent EP 0472 799 AL shows one type of the apparatus for PHT on the market. The apparatus employs a powerful compressor to force air through hollow polyfiber membranes in order to provide an oxygen-depleted gas mixture to the user.

This apparatus has a number of disadvantages including:

high power consumption;

excessive weight—from 100 to 200 lb;

excessive noise level—more than 60–70 db;

inefficiency in that air that is taken in is cooled and dehydratized before compression;

inefficiency in that more gas mixture is generated than actually needed;

the low-oxygen mixture is delivered initially at a high pressure, necessitating apparatus to lower pressure of the delivered gas mixture, such as a receiver-bag;

a gas mixture is delivered to a user under a positive pressure which reduces the rarified mountain-air-effect;

no filter on the air intake opening is employed for removing dust and other particles from the air, causing the membranes to become inoperable too quickly.

All these disadvantages reflect in efficiency of currently available machines.

SUMMARY OF THE INVENTION

A principal object of the present invention is to provide an apparatus for generating oxygen-depleted air simulating an oxygen-impoverished mountain air on different altitudes—preferably from 5,000 to 20,000 ft—which is delivered to a user for periodic hypoxic training or therapy.

A further object of this invention is to provide an apparatus for generating an oxygen-depleted air being delivered to a user where the oxygen content, humidity, and temperature of such air can be regulated depending on a training or therapy protocol and a user's condition by means of manual or computerized logic control.

Another object of the present invention is to provide an apparatus for generating oxygen-depleted air to deliver to a user mixed with medications, aromatic substances, ionized minerals, extracts, herbs and other healing vapors, aerosols, sprays or further remedies and additives.

Yet another object of the present invention is to provide a method for preparing an apparatus for generating oxygen-depleted air from an oxygen enrichment apparatus.

The several embodiments presented here, in employ varying principles for generating an oxygen-depleted gas mixture to deliver to a user for the periodic hypoxic training or therapy which requires air compositions preferably with 7% to 17% of oxygen and 93% to 83% of nitrogen.

The reduction of the oxygen content in the air may be achieved using a membrane gas separation principle to remove a portion of oxygen from ambient air. Alternatively a method of physical or chemical sorption of the oxygen may be used.

Often alternative embodiments generate the low-oxygen mixture by adding to ambient air nitrogen from compressed cartridges or in generated by chemical or physical methods. Further alternative embodiments remove carbon dioxide and other impurities from the gas exhaled by the user in order to make it suitable for reuse.

It is also an object of the invention to provide apparatus equipped with manual or automatic, electronically controlled, regulating, measuring, switching and alarming devices which may be preset by manufacturer, without any need for regulating by the user.

It is further an object of the invention to provide a hypoxic training or therapy device which is portable with the user.

Any of the presented here embodiments can be combined with treadmills or other exercise equipment in order to achieve better results in hypoxic training of athletes and healthy individuals.

DESCRIPTION OF THE INVENTION

The object of this invention is to provide apparatus which simulates an oxygen-depleted mountain air at different altitudes and delivers it to a user at normal atmospheric pressure for periodic hypoxic training or therapy.

The apparatus for supplying oxygen-depleted air may be made by rebuilding an oxygen enrichment apparatus having a membrane separation unit for separating an oxygen-rich permeate delivered through an air-delivery system to a user from an oxygen-depleted retentate being released into the atmosphere.

The rebuilding is accomplished by disconnecting the air-delivery system from the permeate outlet of the separation unit and reconnecting it to the retentate outlet of the separation unit so as to deliver the oxygen-depleted air to a user. If necessary, suitable humidifier and oxygen-content measuring and regulating devices may be added to the apparatus as well.

Figure 1:
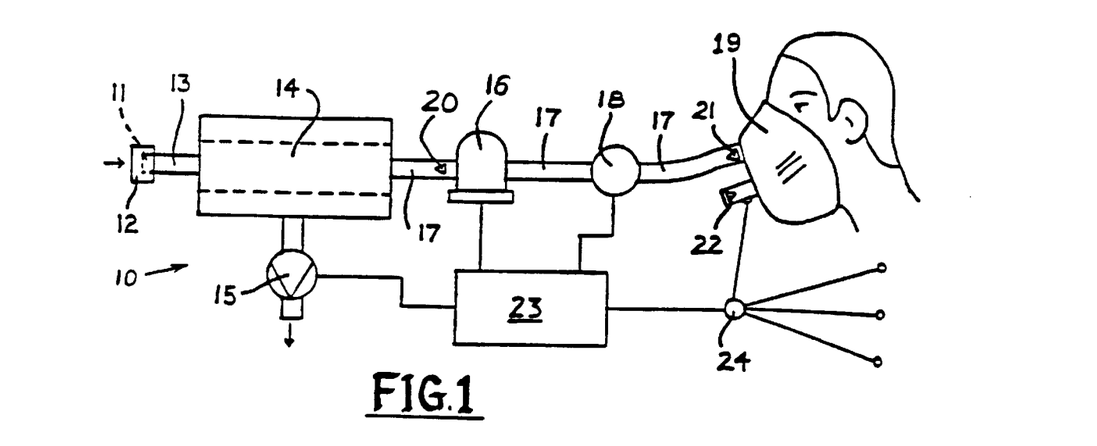
FIG. 1 is schematic view of the apparatus and the invention.

FIG. 1 shows a schematic design of a preferred embodiment. The apparatus 10 employs a membrane gas separation principle. An air intake opening 11 is covered with a disposable, possibly washable, dust filter 12. Intake 11 is connected by a tube or conduit 13 to a membrane separation unit 14. The output of separation unit 14 is connected through air tubings 17 to a humidity-and-temperature-control unit 16, a gas analyzer 18, and finally to the user's respiratory mask 19.

The membrane separation unit 14 is of known construction and may consist of a set of parallel connected membrane cells or single cell which employ either flat or capillary membranes. The inlet of the separation unit 14 receives air form conduit 13, and separates the air across the membrane and delivers the oxygen-depleted retentate gas at as outlet to conduit 17. The separation proceeds responsive to a partial vacuum created by a vacuum pump 15 expelling the oxygen-rich permeate gas mixture as a result of this vacuum pump arrangement, the retentate gas mixture is delivered further to a user under normal atmospheric pressure. Similar membrane separation units, usually with hollow-fiber-polymer membranes, are used currently in the medical oxygen-enriching devices. See, U.S. Pat. No. 3,976,451, U.S. Pat. No. 4,174,955 or U.S. Pat. No. 4,632,677 issued Dec. 30, 1986 to Blackmer, which are herein incorporated by reference. Any of these can be used in the here presented first preferred embodiment.

The particularly preferred material for the membrane is silicone rubber, either flat or capillary, available from Sci-Med, Nikkiso, or Senco-lka. The best membranes are those containing poly(dimethylsiloxane) also referred to as PDMS or its copolymer, or poly[1-(trimethylsilyl)-1-propyne] also referred to as PMSP, available from the Sanyo Chemical Co., the Matsushita Electric Company or the General Electric Co. Also suitable for use in forming the membranes of the present invention are natural rubber, polybutadiene, polystyrene, ethylcellullose, butyl rubber, Teflon-FEP, polyvinylacetate, poly(2,6-dimethylphenylene oxide) or poly(methylpentene-1). Other possible materials will be apparent to those skilled in the art, who will be able to substitute equivalent materials for those enunciated here without departing from the invention.

In the preferred embodiment, membrane cells are made with a porous, tubular shape support structure having a permeable flat sheet membrane layer on the retentate side of the support structure, the membrane layer being preferably from highly permeable organic, synthetic, ceramic, glass, metal, composite, mineral or biologic material, or combinations thereof in symmetric, asymmetric or composite shape, porous or nonporous. Membranes can be prepared in tubular form by joining flat sheets with an appropriate seam or by direct casting onto a cylindrical form. Also suitable are spiral wound membrane configurations and hollow-fiber membranes. Tubular supports are most commonly made of rigid, porous fiberglass. Perforated polymer, composite, ceramic, glass or metal tubes or nonporous tubes containing a grooved liner may also be used effectively.

Due to their kinetic properties, water vapor, carbon dioxide and oxygen penetrate faster than nitrogen through any kind of membranes, which permits a choice of the most permeable membrane under the lowest possible air pressure in order to increase an efficiency of the membrane separation unit 14. The use of a vacuum pump which draws the permeate gas out of the separator greatly reduces the power needed and pressure created compared to the prior art design, which applies compressed air to the intake of the separator.

The vacuum pump 15 for drawing the air through the membrane cells by creating a partial vacuum at their permeate side is also of known construction and is controlled by automatic or manual regulating means which enables the apparatus to achieve a desired oxygen content in the retentate being delivered to a user. The permeate is rich in oxygen and water vapor and may be used first for cooling of the pump 15, and then discharged afterward into the atmosphere. An emergency inhalation mask (not shown) should be kept semi-connected with the discharge opening of the pump 15, ready to use in case of emergency when oxygen-enriched air could be needed.

The humidity and temperature control unit 16 is connected between membrane unit 14 and respiratory mask 19. This unit 16 may be that of any humidity and/or temperature control apparatus, as is well known in the art.

In order to increase an efficiency of the membrane unit 14 a valve means 20 may be incorporated between it and the humidity and temperature control unit 16, preventing the return flow of the humidified gas mixture back into the membrane unit 14. The valve means 20 is preferably to be made as a thin flexible flap which opens when the air movement starts toward a user and closes tightly between the inhalations.

The humidity and temperature control unit 16 consists of a synthetic, metallic, ceramic or composite body having an air intake opening and air exit opening connected with the retentate delivery conduit 17. The body will optimally have a cartridge holder for releasing sterile water or medicated solution inside the unit where it will be released by puncturing the cartridge and subjected to a regulated heating-and-evaporating process in order to warm and humidify the oxygen-depleted retentate incoming into the unit 16 being transmitted to a user for inhalation.

The heat inside the unit 16 may be established by means of electric, infrared, halogen, ultrasonic, and preferably microwave or inductive heating principles.

The valve means 20 could be installed as directly at the air intake opening of the unit 16 for preventing water vapors to flow back into the membrane unit 14.

As an alternative to a cartridge whose contents are evaporated in the humidity control unit 16, a spray dispenser can be installed in the retentate delivery system. The spray dispenser is a device for delivering the contens of a spray can or disposable liquid cartridge inside the unit, where a remedy spray using preferably a nitrogen propellant base may be discharged into the oxygen depleted air being delivered to a user for inhalation. In case of a spray can application, a special discharging means controls the dispensing of the spray or mist from the can in the cartridge holder. In case of a disposable liquid content cartridge a lid or wall of the cartridge is punctured with an intake needle connected to a spray or mist generator.

A gas analyzer unit 18 is connected into the system between the unit 16 and mask 19 in order to measure the oxygen content, humidity, temperature and (optionally) volume of delivered oxygen-depleted gas mixture and send these data to a computerized control unit 23.

The units 14, 16 and 18 are interconnected with air tubing 17 ending through bacterial filter (not shown) with the inhalation mask 19 having a one direction valve 21 which opens for inhalation of the use, and 22 for exhalation.

A set of sensors 24 is provided, depending on the application for measuring cardiopulmonary activities of a user. The sensors 24 are preferably positioned on the users body (i.e. chest, neck, finger, etc.). The data from the gas analyzer 18 and sensors 24 is processed in the computerized control unit 23, which can provide logic control and monitoring of all units and parameters of the system.

A fan means or blower (not shown) may be installed at the air intake opening 11 for additional support of the air movement through the system, if necessary.

The first preferred embodiment employs the regular room air which being drawn through the air intake opening 11 with the dust filter 12 into the membrane separation unit 14 loses its oxygen-and-water-vapor enriched part which is constantly removed by the partial vacuum created by the pump 15 and is immediately replaced by the new incoming air. The oxygen-depleted dry air than moves with each inhalation towards the user's respiratory mask 19 passing through the humidity-and-temperature-control unit 16, where it will be humidified and warmed, and gas analyzer unit 18 which constantly measures the oxygen content, temperature and humidity of the delivered gas mixture sending the data to the computerized control unit 23. An optional volume-meter may be integrated with the gas analyzer for special medical or scientific purposes. A set of sensors 24 provides a constant control of the cardiopulmonary activities of the user sending data to the computerized control unit 23.

The data from the gas analyzer unit 18 and sensors 24 is constantly processed in the computerized control unit 23 which functions independently using it's operating software and provides logic control and monitoring of all operable units and parameters in the system, choosing suitable for the user parameters of the training methodic, including the oxygen content, humidity and temperature of the delivered for inhalation gas mixture, as well the length and number of the hypoxic inhalation cycles and breaks between them. During the breaks between the inhalation cycles and when the user's condition parameters exceed their safety margins the unit 23 turns off the pump 15 and humidifier 16 allowing the regular room air to circulate through the system.

Figure 2:
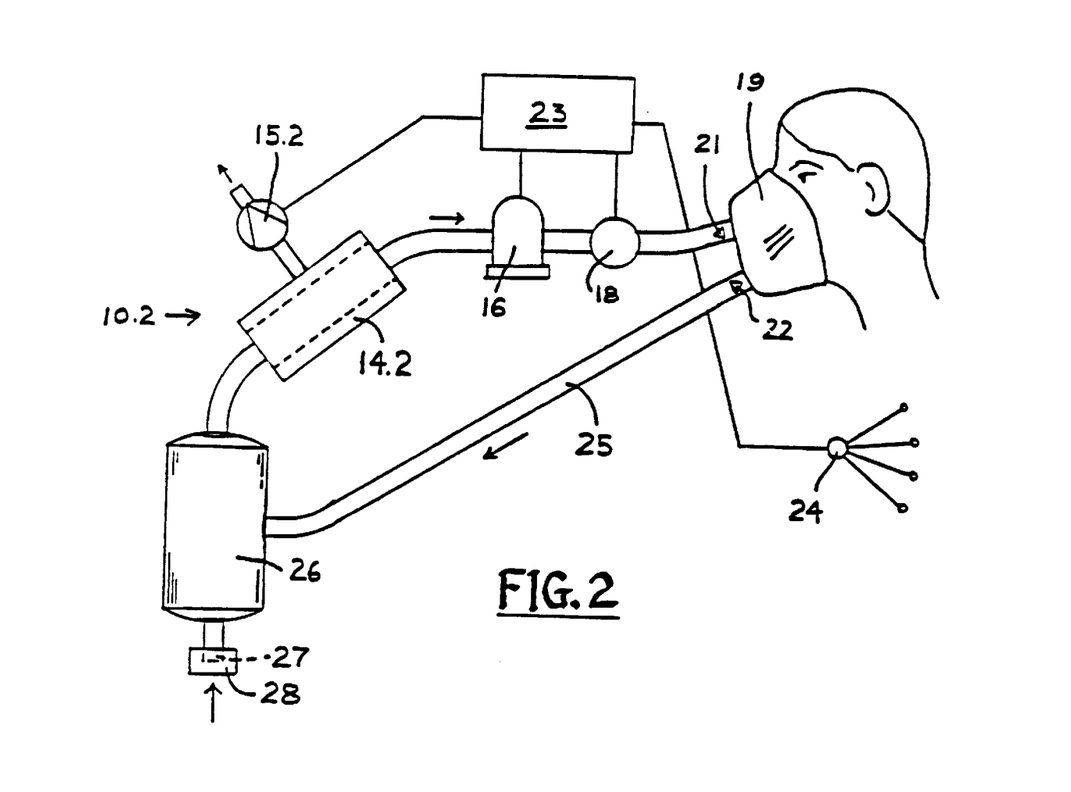
FIG. 2 shows a schematic of an alternate embodiment in the invention wherein the user's exhaled air is recycled to generate a low oxygen gas mixture.
Figure 3:
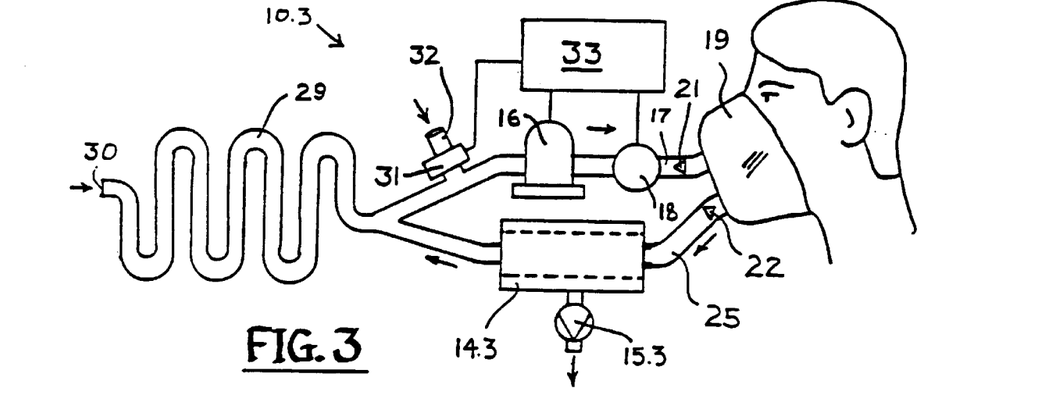
FIG. 3 shows an alternate embodiment of the apparatus of FIG. 2.

FIGS. 2 and 3 show working principles of the second and third embodiments of the apparatus for hypoxic training or therapy which employ a circulation of the gas mixture exhaled by a user in the system in order to significantly lower the power consumption, weight and dimensions of the apparatus.

As shown in the FIG. 2, the second preferred embodiment employs air-preparation-and-delivery-line similar to the first embodiment a consisting of much smaller and less powerful than by the first embodiment membrane separation unit 14.2 with the vacuum pump 15.2, humidity and temperature control unit 16, gas analyzer 18 and mask 19. In this case, the gas mixture exhaled through the valve 22 is delivered through the air tubing 25 to an air mixing vessel 26 which has an air intake opening 27 with dust filter 28 and is connected to the membrane separation unit 14.2

As in the first embodiment, computerized control unit 23 with a set of sensors 24 are employed in the second preferred embodiment 10.2. Alternatively, a manual regulating means (not shown) may be employed instead of the computerized control unit 23 in order to maintain a desired oxygen content in the inhaled gas mixture.

Air exhaled by humans has less oxygen and more carbon dioxide than the usual air at low altitudes which makes it unsuitable for normal reuse. In case of hypoxic training, however, a low oxygen content of the gas mixture is advantageous because it saves the energy for reducing an oxygen content of the using air. However, the higher carbon dioxide content is disadvantageous, and most of it must be removed from the exhaled gas mixture before reuse.

The air exhaled by a human normally has reduced the oxygen content of the inhaled material by approximately 5%, e.g., if a gas mixture of 21% oxygen and 79% nitrogen is inhaled, the exhaled gas will contain approximately 16% oxygen, 5% carbon dioxide and 79% nitrogen. If the gas mixture of approximately 17% oxygen is inhaled the exhaled gas will contain approximately 12% oxygen and 5% carbon dioxide etc. To establish a steady state of equilibrium, then it is necessary to add this 5% oxygen to the recycled gas mixture. As a consequence, the recycled and purified from carbon dioxide gas mixture should be mixed with the ambient air at a ratio of approximately 4:1 to maintain equilibrium of oxygen consumption.

Due to its kinetic properties carbon dioxide penetrates any kind of membrane faster than nitrogen and oxygen which makes it possible to remove it together with the water vapors and a part of the oxygen in the membrane separation unit 14.2, making the exhaled gas mixture perfectly suitable for reuse.

The membrane unit including the membrane types and materials used for partially separating oxygen from the air in the embodiment of FIG. 1 may also be used for separating carbon dioxide and water from the exhaled air from the user. The following materials may also be beneficially used for such a purpose. First, and most preferably are membranes filled with sulforane and poly(ethylene glycol) or aromatic polyimide membranes. Also suitable are membranes made of a material selected from the group consisting of poly[1-(trimethylsilyl)-1-propyne], poly(dimethylsiloxane), poly(2, 6-dimethylphenilene oxide), poly(methylpentene-1), teflon-FE P, polyvinylacetate, ethylcellulose, polystyrene, polypropylene, polyethylene, polyamide, polyacrylate, carbon, butyl rubber, silicon rubber and natural rubber.

The second preferred embodiment has almost a similar working principle, but is more efficient because it employs an exhaled by a user air which is purified from the excessive carbon dioxide and vapors in the membrane separation unit 14.2.

The exhaled gas mixture flows through the one-way valve means 22 and air tubing 25 into the air mixing vessel 26 and, being partially enriched their with the fresh room air, streams into the membrane separation unit 14.2 where the most of the carbon dioxide, water vapors and a part of the oxygen-enriched gas mixture will be removed by the vacuum pump 15.2, being instantly replaced by the incoming from the mixing vessel 26 gas mixture.

The design and functioning of the all other units are similar to the equally numbered units in the first preferred embodiments with the only exception, that the pump 15.2 with the unit 14.2 are much smaller and less productive.

FIG. 3 shows a working scheme of a third preferred embodiment 10.3 employing for reuse exhaled air purified in the membrane separation unit 14.3 and collected in a collector 29 having an opening 30 on one side and connected to the air delivery system on the other side. A fresh-air-supply-device 31 is integrated into the system preferably between the collector 29 and the humidity-and-temperature control unit 16 or gas analyzer 18. This device 31 selectively permits addition of more or less air to adjust the amount of oxygen in the inhaled mixture. The collector 29 is preferably coil-shaped with the air capacity of preferably 1,000 ml or more and having preferably larger diameter tubing than air tubing 17.

The device 31 employs a microprocessor 33 controlled regulating means (not shown) which, changing an air flow capacity, i.e. the section of the air-intake-opening 32, allows addition of a necessary amount of the fresh air into the delivery system for the inhaled gas mixture in order to maintain a desired oxygen content in it. The user may set up the desired oxygen content of the inhaling gas mixture on the apparatus scale in the range from preferably 10% to 17% which activates the microprocessor 33 controlled regulating means of the device 31 constantly receiving data from the gas analyzer unit 18 and instantly changing the air-flow capacity in order to maintain the desired oxygen content. The device most suitable for instant changing of the section of the air-intake opening is widely used in photo-and video cameras as an electronically controlled diaphragm or aperture used for changing of a focal length.

A fan means (not shown) may be installed in the air delivery system between the device 31 and mask 19 for additional support of the air movement through the system, if necessary.

The third preferred embodiment is even more efficient than the second preferred embodiment and employs similar but less productive pump 15.3 with membrane separation unit 14.3 in order to purify an exhaled gas mixture from excessive carbon dioxide, water vapors and other admixtures. A small part of oxygen enriched gas mixture is removed in the unit 14.3 as well. The performance of the pump means 15.3 must allow to make the leaving the unit 14.3 purified gas mixture consisting of preferably 2–7% of oxygen and 98–93% of nitrogen.

The exhaled by a user and purified in the unit 14.3 gas mixture flows into collector 29 freely, because of the opening 30, in the same time mixing with a small part of the outside air and humidifying itself. During the inhalation cycle the gas mixture flows from the collector 29 towards respiratory mask 19 passing connected with the air tubing 17 the fresh-air-supply device 31 and optional units 16 and 18. A disposable airbag placed over intake 30 makes the system more efficient and delivered gas mixture more stabile.

The embodiment of FIG. 3 may be made in a portable version without the units 16, 18, 23 and 24, employing a manual regulating means for changing the air flow capacity in the device 31 (e.g. the section of the air-intake opening 32) according to a factory preset scale of oxygen content from about 10% to 17%.

In this case, the humidity of the delivered for inhalation air will be fully or partially reinstated in the open-ended collector 29 because of the fast permeability of the water vapor. Additionally, in order to reinstate the humidity of the inhalation gas mixture, the air tubing 17 and collector 29 may be made from a porous material highly permeable to water vapor.

The second and third preferred embodiments require much smaller and less productive pumps and membrane separation units which allow light, portable versions to be made for both, stationary and home use, for medical and fitness purposes.

Figure 4:
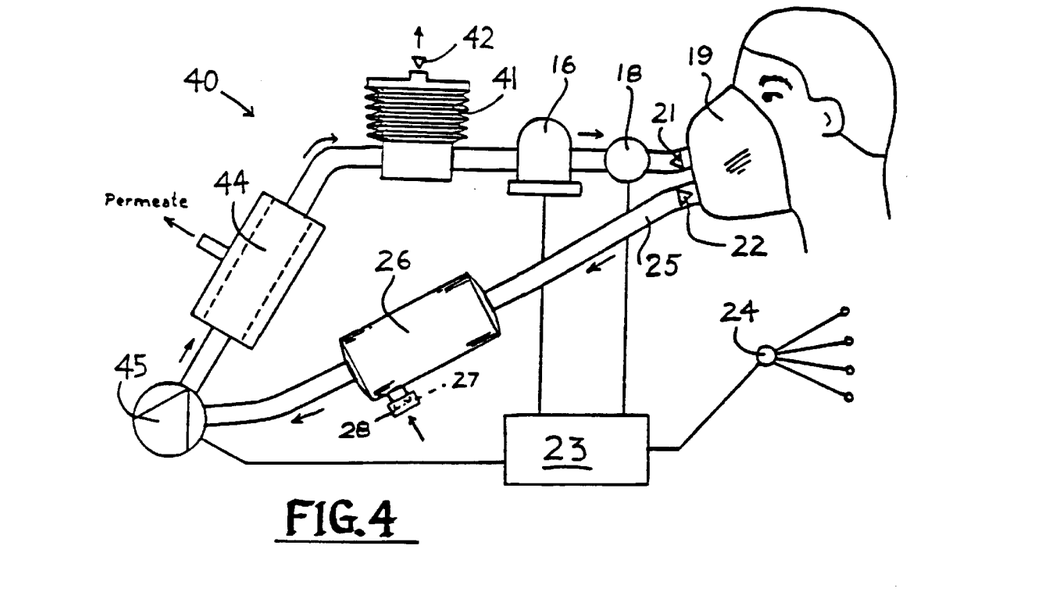
FIG. 4 shows a further alternate embodiment of the apparatus of FIG. 2 with a compressor used therein instead of a vacuum pump.

FIG. 4 shows a working principle of a forth preferred embodiment 40 of the apparatus for hypoxic training or therapy which employs an incoming from the mixing vessel 26 gas mixture compressed by a pump 45 which separates in the membrane separation unit 44 an oxygen-carbon dioxide-and-water-vapor-rich permeate from an nitrogen-rich retentate which is forced into a receiver-vessel 41 and is further delivered through the units 16 and 18 to the respiratory mask 19. The air exhaled by the user flows through the tubing 25 into the mixing vessel 26, being forced by the pump 45 to mix with the incoming fresh air from the air-intake opening 27.

The membrane separation unit 44 is designed to let cause compressed gas mixture to partially permeate membrane cells, discharging the permeate into the atmosphere and forcing the nitrogen-rich retentate into the receiver-vessel 41 equipped with safety valve 42. The receiver-vessel 41 is made preferably from flexible or elastic material and is able to change in volume in order to hold the delivered gas mixture under low, almost normal atmospheric air pressure which may be easy regulated by the safety valve means 42.

The fourth preferred embodiment 40 employs exhaled by a user gas mixture which being mixed with the fresh air in the mixing vessel 26 is compressed by the pump means 45 in order to separate water-vapor-carbond-oxide-and-oxygen-enriched permeate from the oxygen-depleted retentate in the membrane separation unit 44. The permeate is discharged into the atmosphere and the retintate is forced under pressure into pressure equalizing receiver 41 which is able to increase it's volume in order to lower the pressure of the retintate and keep the gas mixture under the constant low pressure employing the safety valve means 42. If the gas mixture pressure increases above the preset by the manufacturer safety level the safety valve opens and excessive volume of the gas mixture is discharged into the atmosphere. The gas mixture is further delivered under the constant low pressure to the user passing by the humidity control unit 16 and gas analyzer 18. The performance of the whole system is constantly controlled by the computerized control unit 23.

Figure 5:
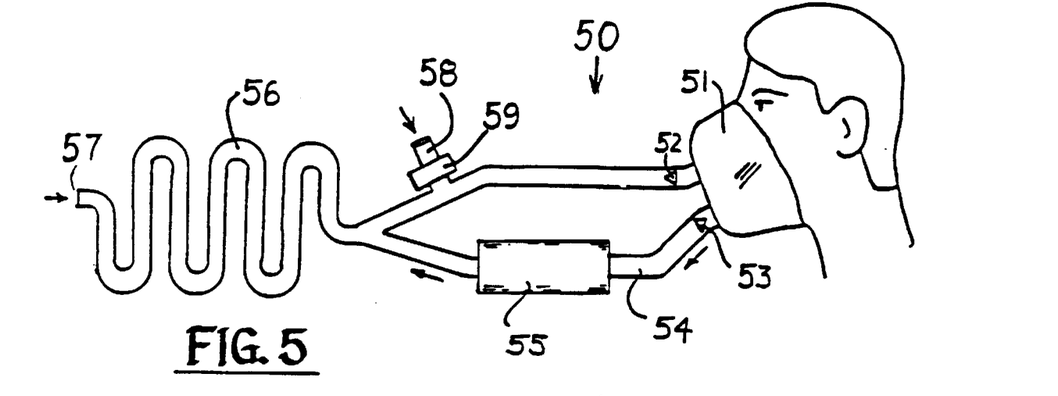
FIG. 5 shows a further alternative embodiment wherein the carbon dioxide of the user's exhaled breath is extracted by an adsorption apparatus.

FIG. 5 shows a working scheme of the fifth preferred embodiment 50 of the apparatus for hypoxic training or therapy which employs a principle of physical absorption, adsorption or chemisorption of the carbon dioxide from the gas mixture exhaled by a user and being reused for inhalation.

Apparatus 50 consists of a respiratory mask 51 with an inhalation valve 52 and an exhalation valve 53, air tubing 54, a disposable adsorption cartridge 55, a gas mixture collector 56 with an open end 57. A collector 56, made preferably in coil shape is connected through the air tubing 54 to the inhalation valve 52. The inner coil section of collector 56 is preferably larger than by air tubing 54. A fresh-air-intake-device 58 having a regulator 59 is integrated into the system between the collector 56 and mask 51 in order to add a necessary amount of the room air to reused gas mixture. A disposable airbag may be used as extention or instead of collector 56 for collection of the recycled gas mixture.

Regulator 59 may be made as a microprocessor 33 controlled and combined with the gas analyzer 18 automatic device (see FIG. 3) in order to receive oxygen-content data constantly and maintain the stability of the gas mixture. In the shown embodiment 50, which is mainly for home or fitness use, a manual regulator 59 is preferably made with the factory preset oxygen content scale of from about 10% to about 17%. In order to equalize the humidity of the gas mixture delivered through the system, the collector 56 and tubing 54 may be made from a porous material allowing the water vapor to permeate their walls.

The disposable adsorption cartridge 55 is designed to let the air exhaled by a user pass unhindered through it, adsorbing at the same time most of the carbon dioxide and making the gas mixture suitable for reuse. The solid or liquid substances of the $CO_2$-sorption process inside the cartridge 55 may be of physical, chemical, biological or other origin—there are many suitable chemicals, substances and technologies available at the present time for this purpose, as are well known by those skilled in the art. Preferred materials for carbon dioxide adsorption are selected from the group consisting of natural and synthesized molecular sieve zeolites and carbon molecular sieves available from Bergbau-Forschung GmbH in West Germany and Takeda Chemical Company in Japan. Also suitable for use as adsorbents are activated carbon, silica gel, pillared interlayer clays, $AlPO_4$ molecular sieves and ethanolamines.

Cartridge 55 must be able to adsorb most of the carbon dioxide for 5 to 20 minutes, which is usually a total time of the employing of the system per session.

The cartridge 55 preferably is equipped with an indicator (not shown) which prevents accidental reuse of the already depicted cartridge. The indicator may employ a chemical, physical or biological process to produce a visual or audible signal when the cartridge is finished, or the indicator may alternatively make the system inoperable.

Taking into account that a periodic hypoxic training course consist usually of 20 sessions from 10 to 60 minutes each with decreasing oxygen-content-level in the periodically inhaled air preferably from 10% to 17%, a set of 20 different numbered adsorbing cartridges should be manufactured and supplied for different use, from inactive home respirations to superactive physical training, which requires cartridges with different adsorbing capacities.

The apparatus 50 or preferably disposable cartridges 55 should be equipped with an electronic timer (not shown) which signals during the training session when the mask 51 should be taken off or put back on (e.g. training cycles with 3 minutes of inhalation of hypoxic gas mixture and 5 minutes rest i.e. normal respiration without the mask).

The apparatus 50 is preferably to be made as a portable version to carry on the athlete's body, e.g. in a kind of a rucksack or installed in a helmet, or may be combined with any kind of exercise equipment, such as tread mills, bicycles, etc. The mask 51 should be made preferably to hand held, without any straps, which makes withdrawal of the apparatus 50 from the face of the user easy, if necessary.

The preferred embodiment 50 has the same as the third preferred embodiment 10.3 working principle with the only exception that instead of the membrane separation unit 14.3 with the vacuum pump 15.3 an adsorption cartridge 55 is employed in order to remove excessive carbon dioxide from the exhaled gas mixture, making it suitable for reuse.

The exhaled by a user gas mixture flows through the one-way valve means 53 and tubing 54 into an adsorption cartridge 55 where the most of the carbon dioxide is adsorbed. The purified gas mixture than flows into an open-ended collector 56 partially mixing with the outside air incoming through the opening 57. During the inhalation cycle the gas mixture flows to a user's mask 51 passing the fresh-air-supply device 59 and optional gas analyzer.

Figure 6:
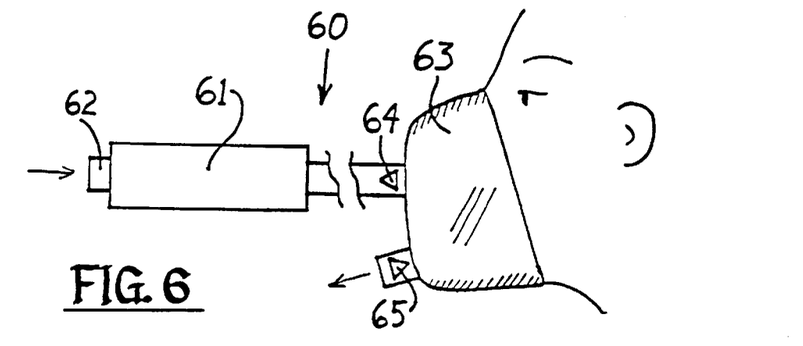
FIG. 6 shows an alternate embodiment of the apparatus of FIG. 1 wherein ambient air is taken in and the oxygen depleted by a chemical or other method for supplying to the user.

FIG. 6 shows the working principle of a sixth preferred embodiment of the apparatus for periodic hypoxic training. The embodiment 60 employs a principle of chemical or physical sorption or consumption (e.g. by electric incandescence) of the oxygen from the ambient air, and comprises an oxygen-depleting cartridge 61 receiving air from an air-intake opening 62 supplying the oxygen-depleted air to a respiratory mask 63. A nitrogen-producing cartridge may be used instead of the oxygen-depleting cartrige 61.

The disposable cartridge 61 is designed to let ambient air pass unhindered therethrough, adsorbing preferably about 20 to 50% of oxygen, which yields air with about 10 to 17% oxygen content to be inhaled by a user for hypoxic training. The cartridge 61 holds inside an adsorbing substance of solid or liquid form, or an oxygen consuming device employing any known suitable method of oxygen consumption (e.g. electrical incandescence, adsorption process by zeolites or oxidation process) as will be understood by one of skill in the art. Most preferred adsorbents are selected from the group consisting of molecular sieve zeolites and carbon molecular sieves.

Figure 6A:
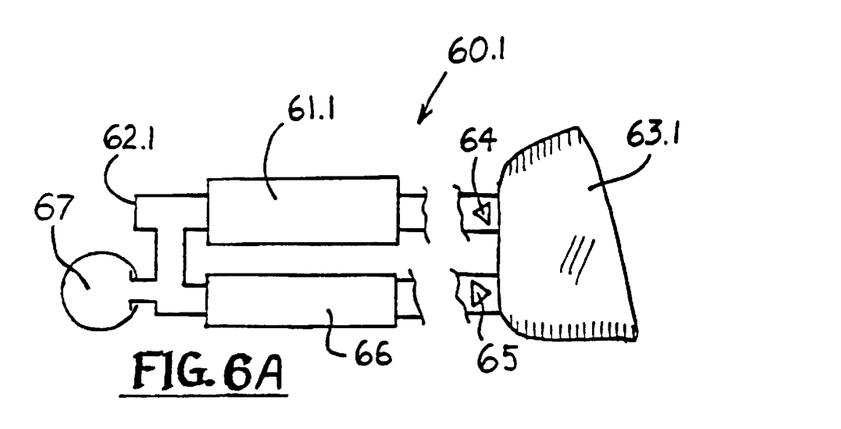
FIG. 6a shows an alternate embodiment of the apparatus of FIG. 6 wherein sorption methods are used to remove carbon dioxide from recycled exhaled air of the user and to reduce the oxygen content of the mixture of this with air taken from the environment.

FIG. 6a shows an apparatus as in FIG. 6, but wherein exhaled air is recycled through carbon dioxide adsorption unit 66 and collected in the airbag or balloon 67 (shown inflated) and is mixed with fresh air taken in through the inlet 62. 1, and then passed through oxygen-adsorption unit 61.1 to again yield a low-oxygen gas mixture. The disposable airbag 67 is preferably made of a thin flexible or elastic material selected from the group consisting of paper, fabric, natural or silicon rubber or other polymers. The inlet 62.1 is equipped with a manual or electronically controlled regulating device (not shown) with a valve preferably made as a thin flexible flap which opens when the air movement starts toward a user and closes tightly between inhalations.

The working principle of the sixth preferred embodiment 60 is quite simple: the outside air is drawn by the user's inhalation into the oxygen-depleting cartridge 61 where it looses a necessary amount of oxygen before being delivered to a user. The alternate embodiment 60.1 employs additionaly carbon dioxide adsorbing cartriges in order to recycle exhaled air which is reused in the system.

Figures 7, 8, 9:
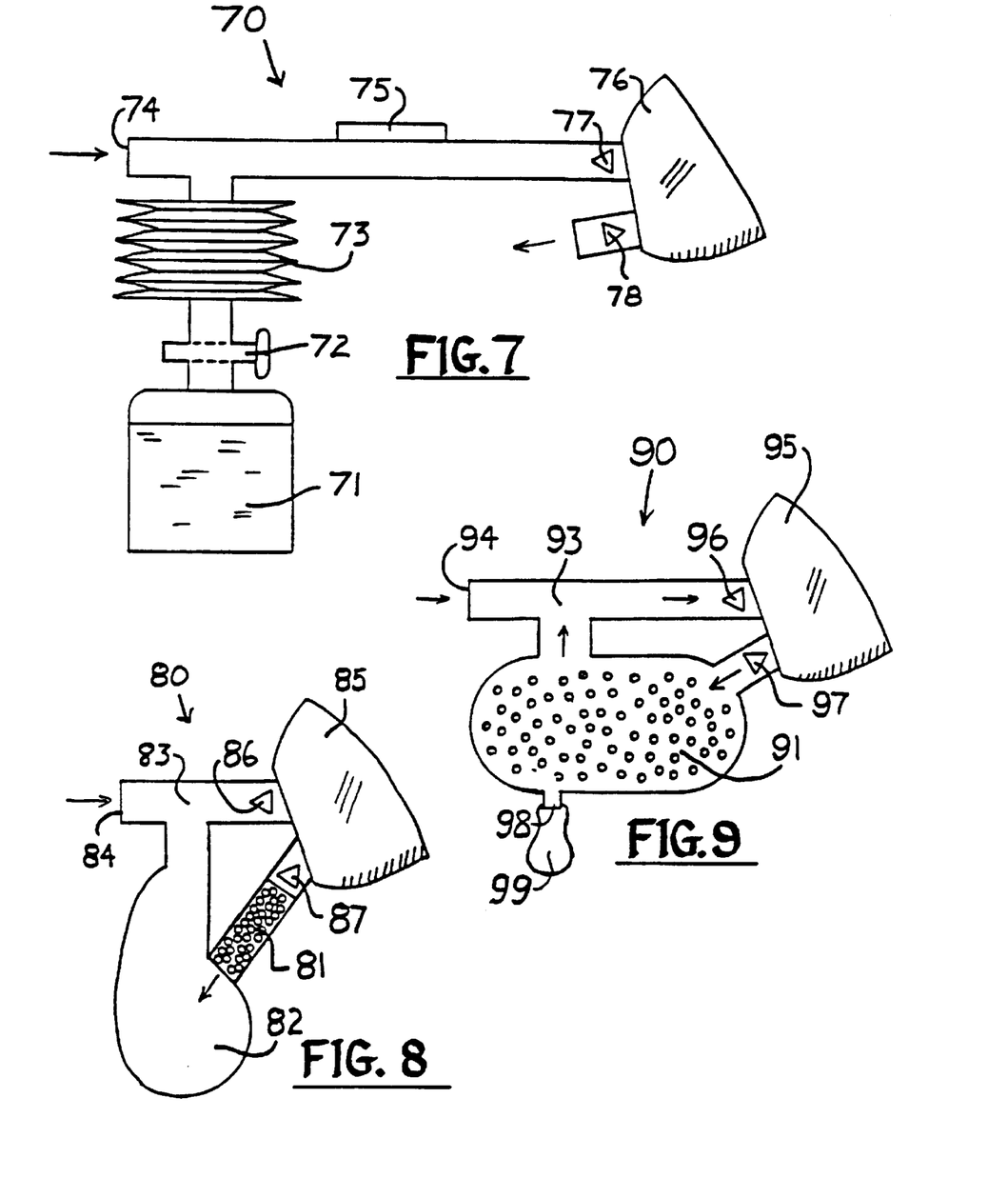
FIG. 7 shows a further alternate embodiment wherein nitrogen or a low oxygen gas mixture is mixed with fresh air being taken in from the surrounding atmosphere.
FIG. 8 shows an alternate embodiment wherein carbon dioxide is extracted by a chemical method from the user's exhaled air and mixed with ambient air to yield low oxygen air for continued breathing.
FIG. 9 shows an alternate structural embodiment of the device of FIG. 8.

A working scheme of the seventh preferred embodiment is shown in FIG. 7. The embodiment 70 employs a container 71 of nitrogen which is mixed in necessary proportions with room air to maintain a desired oxygen content in the air being delivered to a user for inhalation. Nitrogen (or oxygen depleted air which may be used instead of nitrogen) may be held in compressed, liquid or dissolved (e.g. in liquid, gel, porous metal, zeolites, molecular sieve carbon or other solid substances) form suit able to be released by regulating means 72 in desired quantities. The released nitrogen flows into a pressure equalizing receiver 73 and is mixed in desired proportions with the fresh air coming in through the regulatable air-intake opening 74 being delivered further to the respiratory mask 76 for use under normal atmospheric pressure. The manual or automatic., microprocessor controlled, oxygen content regulator 75 enables to maintain stable gas mixture with necessary parameters. The intake 74 is equipped with a valve preferably made as a thin flexible flap which opens when the air movement starts toward a user and closes between inhalations.

The design of all necessary equipment and devices is well known and used for decades in scuba diving and medical respiratory equipment.

The eighth embodiment shown in FIG. 8 employs physical or chemical adsorption of carbon dioxide from the user exhaled gas mixture in order to make it reusable. The exhaled air flows through the valve 87 and disposable $CO_2$-adsorption cartridge 81 into receiver-bag 82 whereby most of the carbon dioxide is adsorbed making the exhaled gas mixture reusable. The reusable gas mixture flows with each inhalation cycle into the mixing chamber 83, and is mixed with the incoming fresh air from the air-intake opening 84 and delivered to a user through an inhalation valve 86 of the respiratory mask 85. The disposable adsorption cartridge 81 is filled with the solid or liquid $CO_2$-sorption substance and allows the exhaled gas mixture to pass through unhindered while the $CO_2$ is extracted therefrom. The disposable receiver-bag 82 may be made from a thin airtight flexible, or elastic material selected from the group consisting peferably of paper, rubber, fabric and polymers. A manual regulating means (not shown) for changing the air flow capacity is installed at the air-intake opening 84 with the factory-preset oxygen-content scale. The intake 84 is equipped with a valve preferably made as a thin flexible flap which opens when the air movement starts toward a user and closes tightly between the inhalations. The disposable cartrige 81 is equipped with an indicator (not shown) which prevents accidental reuse of the already depicted cartrige.

The ninth preferred embodiment employs the same idea with the only difference that the carbon dioxide adsorbing substance is situated directly in the disposable receiver container 91. The air exhaled through the valve means 97 and purified from carbon dioxide in the receiver 91 flows with each inhalation into the mixer 93 and is mixed with the incoming fresh air from the air-intake opening 94 and is delivered through the valve means 96 to a user's respiratory mask 95. A manual regulator for changing the air flow capacity (not shown) is installed at the air-intake opening 94 with the factory-preset oxygen-content scale. An additional, similar to 67 (FIG. 6.1), disposable airbag 99 (shown deflated) should be installed at the opening 98 for collection of reusable gas mixture. The intake 94 is also equipped with a flap which opens when the air movement starts toward a user and closes between the inhalations.

What is claimed is:

1. An apparatus for supplying a low oxygen gas mixture to a user, said apparatus comprising an oxygen reducing apparatus communicating with the ambient atmosphere and receiving air therefrom, and an outlet supplying air having an oxygen concentration lower than that of the ambient atmosphere; and a breathing device having an inlet structure communicating with the outlet of said oxygen reducing apparatus and supplying said reduced oxygen air to said user to breathe;

said oxygen reducing apparatus including a separating unit defining therein an interior space, and having therein a membrane structure separating said interior space into a retentate space and a permeate space;

said separating unit having a gas inlet receiving air from the ambient atmosphere and communicating with said retentate space, a retentate outlet communicating with said retentate space and with said outlet of said oxygen reducing apparatus, and a permeate outlet communicating with said permeate space; and a vacuum pump device connected with said permeate outlet and drawing gas from said permeate space and causing separation of gas entering the retentate space, said vacuum pump device drawing said gas so that said separating unit yields at said retentate outlet an air mixture having an oxygen content of about 7 to 17%; and said breathing device further having an outlet structure transmitting air exhaled by the user; and air transmitting means receiving said exhaled air and transmitting the exhaled air to the gas inlet of the separating unit so that said exhaled air is separated in the separating unit together with air received from the external environment.

2. The invention according to claim 1 and said membrane being generally cylindrical and defining said retentate space to be a generally cylindrical space and said permeate space to be a space surrounding the cylindrical space.

3. The invention according to claim 1 and said membrane structure including a membrane supported on a generally cylindrical structure and defining said permeate space to be a generally cylindrical space and said retentate space to be a space surrounding said permeate space.

4. The invention according to claim 1 and said membrane being generally a hollow-fiber-polymer membrane.

5. The invention according to claim 1 and said membrane being formed of material selected from the group consisting of organic, metal, ceramic, glass, mineral, synthetic and composite materials.

6. The invention according to claim 1 and said membrane being made of a material selected from the group consisting of poly[1-(trimethylsilyl)-1-propyne], poly (dimethylsiloxane), polyethylene, polypropylene, polystyrene, ethylcellulose, polyvinylacetate, Teflon-FEP, poly(2,6-dimethylphenilene oxide), poly(methylpentene-1), carbon, zeolites, natural rubber, butyl rubber and silicon rubber.

7. The invention according to claim 1 and said oxygen content reduction system further comprising a humidifier and heater unit communicating with the retentate outlet of said separating unit and selectively adding water vapor and heat to said reduced oxygen air and transmitting said reduced oxygen air to said breathing device.

8. A device for supplying a gas mixture having a reduced oxygen content relative to the ambient air, said device comprising a gas preparation system communicating with the surrounding atmosphere and receiving air therefrom, said gas preparation system including an outlet supplying a reduced-oxygen gas mixture having an oxygen content lower than that of the air received from the surrounding atmosphere;

and a breathing device having an inlet connected with the outlet of said gas preparation system and receiving therefrom said reduced-oxygen gas mixture and supplying said reduced oxygen gas mixture to a user to breathe;

said gas preparation system including a mixing structure defining a space therein and having first and second mixing inlets and a mixing outlet communicating with said interior space, said first mixing inlet being operatively associated with the surrounding atmosphere and receiving air therefrom;

said mixing outlet communicating with said breathing device inlet and supplying said reduced oxygen gas mixture thereto to be breathed by the user;

said breathing device further comprising an outlet structure transmitting air exhaled by the user; and a gas transmitting structure receiving said exhaled air and transmitting said exhaled air to said second mixing inlet.

9. The invention according to claim 8 wherein at least a portion of said gas preparation system is made of porous material which is highly permeable with respect to water vapor.

10. The invention according to claim 8 and the device supplying reduced oxygen air comprising an oxygen extraction system receiving ambient air and removing at least a portion of oxygen therefrom and transmitting the reduced oxygen content air to said breathing device;

said oxygen extraction system comprising an oxygen sorption unit containing material that adsorbs oxygen from air passing therethrough.

11. The invention according to claim 8 and said gas transmitting structure including a gas extraction device that removes carbon dioxide from said exhaled air before it is transmitted to said second mixing inlet.

12. The invention according to claim 11 and said gas extraction device including a membrane separator having a membrane therein through which carbon dioxide passes more quickly than nitrogen.

13. The invention according to claim 8 and said gas preparation system further comprising a gas separating system receiving said reduced oxygen mixture from said mixing outlet, said gas separating system removing carbon dioxide and oxygen from said reduced oxygen mixture so that the remaining mixture has an oxygen content of about 7 to 17%.

14. The invention according to claim 13 and said gas separation system including a membrane separator having a membrane therein through which carbon dioxide and oxygen pass more quickly than nitrogen.

15. The invention according to claim 14 and said membrane defining in said membrane separator a permeate space and a retentate space, and said membrane separator further having a vacuum pump operatively associated with said permeate space and drawing gas therefrom so as to cause separation of carbon dioxide and oxygen from said reduced oxygen mixture through said membrane.

16. A device for supplying a gas mixture having a reduced oxygen content relative to the ambient air, said device comprising a gas preparation system communicating with the surrounding atmosphere and receiving air therefrom, said gas preparation system including an outlet supplying a reduced-oxygen gas mixture having an oxygen content lower than that of the air received from the surrounding atmosphere;

and a breathing device having an inlet connected with the outlet of said gas preparation system and receiving therefrom said reduced-oxygen gas mixture and supplying said reduced oxygen gas mixture to a user to breathe;

said gas preparation system including a mixing structure defining a space therein and having first and second mixing inlets and a mixing outlet communicating with said interior space, said first mixing inlet being operatively associated with the surrounding atmosphere and receiving air therefrom;

a device supplying a low oxygen gas mixture which is lower in oxygen content than the ambient atmosphere being connected with said second mixing inlet; and said mixing outlet communicating with said breathing device inlet and supplying a said reduced oxygen gas mixture thereto to be breathed by the user;

said breathing device having an outlet, said breathing device inlet being equipped with an inlet valve structure which permits only intake of gas there through into the breathing device and said outlet being equipped with an outlet valve structure which permits only the flow of exhaled gas therethrough out of the breathing device;

the device supplying reduced oxygen gas mixture comprising a carbon dioxide extraction system receiving exhaled gas from the outlet of the breathing device and removing at least a portion of carbon dioxide therefrom and transmitting the reduced carbon dioxide gas to the mixing structure.

17. The invention according to claim 16 and said carbon dioxide extraction system comprising a carbon dioxide sorption unit containing material that removes carbon dioxide from gas passing therethrough employing process selected from the group consisting of physical adsorption, absorption and chemisorption.

18. The invention according to claim 17 and said material for carbon dioxide sorption being selected from the group consisting of natural and synthetic molecular sieve zeolites, carbon molecular sieves, activated carbon, silica gel, pillared interlayer clays, $AlPO_4$ molecular sieves and ethanolamines.

19. The invention according to claim 16 and said carbon dioxide extraction system comprising a separating unit defining therein an interior space and having therein a membrane dividing said interior space into a permeate space and a retentate space, said separating unit having an extraction unit outlet and an extraction unit inlet communicating with said retentate space; and a permeate outlet communicating with said permeate space.

20. The invention according to claim 19 and said extraction permeate outlet being connected with a vacuum pump drawing gas from said permeate space and causing extraction from gas entering said retentate inlet of at least a portion of the carbon dioxide therein.

21. The invention according to claim 19 and said membrane being made of a material selected from the group consisting of silicone rubber, natural rubber, butyl rubber, poly(ethylene glycol), polyacrylate, polyamyde, polyethylene, polypropylene, polystyrene, ethylcellulose, polyvinylacetate, Teflon-FEP, poly[1-(trimethylsilyl)-1-propyne], poly(dimethylsiloxane), poly(2,6-dimethylphenilene oxide) and poly(methylpentene-1).

\* \* \* \* \*